(12) United States Patent
Bethi

(10) Patent No.: US 8,715,234 B2
(45) Date of Patent: May 6, 2014

(54) DEVICE FOR LOCATING EPIDURAL SPACE WHILE SAFEGUARDING AGAINST DURAL PUNCTURE THROUGH DIFFERENTIAL FRICTION TECHNIQUE

(75) Inventor: Ravindar Bethi, Andhra Pradesh (IN)

(73) Assignee: B. Braun Melsungen AG, Melsungen (DE)

( * ) Notice: Subject to any disclaimer, the term of this patent is extended or adjusted under 35 U.S.C. 154(b) by 384 days.

(21) Appl. No.: 12/999,473

(22) PCT Filed: Jun. 12, 2009

(86) PCT No.: PCT/IN2009/000340
§ 371 (c)(1),
(2), (4) Date: Jan. 10, 2011

(87) PCT Pub. No.: WO2009/153807
PCT Pub. Date: Dec. 23, 2009

(65) Prior Publication Data
US 2011/0118702 A1    May 19, 2011

(30) Foreign Application Priority Data

Jun. 19, 2008   (IN) .......................... 1491/CHE/2008

(51) Int. Cl.
*A61M 5/00*   (2006.01)

(52) U.S. Cl.
USPC ........................................................ 604/117

(58) Field of Classification Search
USPC .............................................. 604/117, 121
See application file for complete search history.

(56) References Cited

U.S. PATENT DOCUMENTS

| | | | |
|---|---|---|---|
| 4,175,567 A | 11/1979 | Patel | |
| 4,414,983 A | 11/1983 | Evans et al. | |
| 4,919,653 A | 4/1990 | Martinez et al. | |
| 5,104,382 A | 4/1992 | Brinkerhoff et al. | |
| 5,205,828 A | 4/1993 | Kedem | |
| 5,836,914 A | 11/1998 | Houghton | |
| 5,902,273 A | 5/1999 | Yang et al. | |
| 6,773,417 B2 | 8/2004 | Fitzgibbons et al. | |
| 7,175,608 B2 | 2/2007 | Hasan et al. | |
| 8,197,443 B2 * | 6/2012 | Sundar et al. | ............... 604/121 |

FOREIGN PATENT DOCUMENTS

| | | |
|---|---|---|
| ES | 8706023 | 8/1987 |
| GB | 2226496 | 7/1990 |
| MX | 9603835 | 3/1997 |
| WO | WO 03/057282 | 7/2003 |
| WO | WO 2005/004947 | 1/2005 |

OTHER PUBLICATIONS

International Search Report for PCT/IN2009/000340 mailed Dec. 15, 2009.

* cited by examiner

*Primary Examiner* — Kevin C Sirmons
*Assistant Examiner* — Deanna K Hall
(74) *Attorney, Agent, or Firm* — RatnerPrestia

(57) ABSTRACT

A device for locating a cavity within two walls including a syringe including a syringe piston slideable in a first syringe barrel for discharging air or fluid contained in the first syringe barrel on forward movement of the syringe piston into the cavity, the first syringe barrel being attached to a hub of a needle cannula; and a frame which at least in part encases the syringe and which is solely connected to the back of the syringe piston.

9 Claims, 20 Drawing Sheets

*Prior- art*

*Prior-art*

Prior-art

Prior-art

DEVICE FOR LOCATING EPIDURAL SPACE WHILE SAFEGUARDING AGAINST DURAL PUNCTURE THROUGH DIFFERENTIAL FRICTION TECHNIQUE

CROSS REFERENCE TO RELATED APPLICATIONS

This application is the U.S. national phase application of PCT International Application No. PCT/IN2009/000340, filed Jun. 12, 2009, which claims priority to Indian Patent Application No. IN 1491/CHE/2008 filed Jun. 19, 2008, the contents of such applications being incorporated herein by reference.

FIELD OF THE INVENTION

The present invention relates to an epidural space locating device which as well prevents dural puncture in the spinal column of vertebrates and, more particularly, of a modification in currently known epidural space locating systems which allows the anaesthetists to properly locate by injecting the air or saline into the epidural space in the process of injecting certain drugs and for passing a catheter for same purpose.

BACKGROUND OF THE INVENTION

In medical practice, identification of epidural space is required for therapeutic, anaesthetic and diagnostic procedures.

The currently used techniques rely on high level of manual skill and dexterity and require specialised training. These techniques are not uncommonly associated with technical difficulties or complications.

In the conventional method; anaesthetist uses his/her skill in locating the epidural space by injecting the air or saline into the epidural space. The anesthetist ensures that the patient stays in the proper position while locating the space. In the spinal column, once the tip of the epidural needle just enters the deeper part of interspinous ligament, the needle is held in place. A saline or air filled syringe is attached tightly to the hub of the needle. The epidural needle is advanced holding its shaft or wings mounted on the hub of the needle. A constant pressure is built up in the syringe by manual compression of piston. Once the tip of the epidural needle enters the epidural space, the anesthetist feels sudden loss of friction enabling him to inject the pressurised saline to confirm the position in the epidural space. This method is depicted through the FIG. 1.

The main disadvantage of this procedure is, it takes longer to establish the space and technically more demanding.

To overcome this disadvantage there are several methods or devices that have been invented and adopted. While so, each inventor claims his device and method having simpler technology, user friendly and most advanced.

U.S. Pat. No. 7,175,608 (Maan Hasan et al.,) teaches the working and construction of a device for locating the epidural space. The device includes a diaphragm that is adapted for pressurization. The diaphragm bulges outwards when the device is pressurized. Also, the device is adapted to connect a needle. In some embodiments the device is pressurized with air or saline. In some other embodiments the device includes an injection port for injection of pressurized fluid. This device is depicted in FIG. 2 hereof.

U.S. Pat. No. 6,773,417 (James F. Fitzgibbons et al.,) teaches the working and construction of the device for locating the epidural space. The epidural space locating device comprises a first end and a second end and a longitudinal passage way extending there through, the first end of which is coupleable to a luer assembly; and a collapsible bellows camber having one end coupled to the other end of the body section and other end exposed so as to permit pressure to be exerted thereon by one or more digits of a hand, wherein positive pressure within the bellows chamber maintains the integrity of the shape of the bellows chamber and wherein negative or zero pressure within the bellows chamber facilitates the collapsing of the shape of the bellows chamber thus indicating the locating of the epidural space by a needle that is coupled to the luer assembly; wherein the loss of pressure within the bellows chamber is sensed by the one or more digits of the hand as the shape of the bellows chamber collapses. This device is depicted in FIG. 3 hereof.

U.S. Pat. No. 5,902,273 (Ian Y Yang et al.,) teaches the working and construction of the device for locating the epidural space. According thereto, a syringe that can be positively pressurized via a one-way valve and illustrated by a pressure indicator is designed to be used with an epidural needle to identify epidural space and to protect the dura being punctured when a loss of positive pressure occurs. The inventive syringe housing having a plunger with a longitudinal bore for pressurization is connected to a pressure chamber via the one-way valve allowing air flow only into the pressurization chamber from the syringe housing. A needle is air-tightly connected to the pressurization chamber with a needle connecting device. A pressure indicator connected to the pressurization chamber objectively indicates the loss of positive pressure when the needle enters the epidural space. The positively pressurized air from the needle deflects the dura away from the needle tip' and prevents dural puncture. This device is depicted in FIG. 4 hereof.

U.S. Pat. No. 4,919,653 (Antonio E. Martinez et al) teaches the working and construction of device for locating the epidural space: According thereto, the device consists of a cannula constituted of a supporting body and a pipe. There exists a magnet surrounding a sleeve in the axial direction and positioned at the back part of the supporting body in the supporting body. When a catheter is inserted into the back of a patient and reaches the epidural cavity, its vacuum condition is sensed by means of a pressure sensor and the magnet and an alarm are actuated. This device is depicted in FIG. 5 hereof.

U.S. Pat. No. 4,175,567 (Bhupendra C, Patel) teaches the working and construction of the device for locating the epidural space. According thereto is method of locating the epidural space in a patient's body with a needle assembly having a flexible film defining a closed cavity which communicates with a needle of the assembly, comprising the steps of positioning a tip of the assembly adjacent the epidural space, and advancing the assembly into the body while determining whether the film flexes inwardly or outwardly relative to the assembly to ascertain the position of the needle assembly tip in the patient's body. This device is depicted in FIG. 6 hereof.

W005004947 (Bryan Vincent E. et al.,) teaches the working and construction of device for locating the epidural space. According thereto, a system for grasping, holding, stabilizing, and selectively releasing tissue with minimal damage to the tissue is disclosed. The system can further include a device that signals entry into the epidural space. A tubular member is provided having at a distal tip an annular surface surrounding a terminal port and at least one barb projecting at an angle from the annular surface for grasping and controlling the tissue. Each barb is formed having a sharp edge configured to grasp the tissue as the tubular member is rotated about its longitudinal axis. One implementation of the system includes a plurality of unidirectional barbs spaced around the annular surface. The system can further include an indicator mechanism that gives a visual and a tactile indication of when the tubular member, such as a cannula, encounters and penetrates tissue. The system facilitates the appropriate placement of a n epidural or subdural catheter or patch of any kind. This device is depicted in FIG. 7 hereof.

MX9603835 (Federick C. Houghton) teaches the working and construction of device for locating the epidural space. According thereto, a regulating device for variably regulating the length of a combined spinal epidural needle and the method of practising the same is disclosed. In one variant, the regulating device features a pair of substantially concentricity disposed sliding members to which each of the epidural needle and spinal needle may be separately fitted. A spring element is provided to selectably engage the spinal needle. The spring element includes one end fixed to the sliding member securing the epidural needle, a free end manipulable by a user, and at least one passage or opening disposed between the fixed and free ends through which the spinal needle passes. The opening is configured to permit either gripping or free sliding of the spinal needle depending on the practitioner's actuation of the spring element. By actuation of the spring element, the practitioner may control axial movement between the sliding members, thereby regulating the extension of the spinal needle relative to the epidural needle. The sliding members may be configured in a variety of shapes or dimensions to accommodate various combinations of spinal and epidural needles. The device may be provided pre-assembled with either one or both of the spinal needle or epidural needle, or it may be employed with a spinal needle, epidural needle, or both separately sourced. This device is depicted in FIG. 8 hereof.

U.S. Pat. No. 5,205,828 (Kedem Dan) teaches the working and construction of device for locating the epidural space. According thereto, the stilette is connected at its posterior end to a displaceable piston located in the syringe. The piston, which is constrained to move between two fixed points of pre-selected separation, is immobilized in its posterior position by a latch. Means are provided for biasing the piston anteriorly.

In another embodiment thereof, the device is accomplished by connecting the anterior piston to a biasing piston by a spring. The biasing piston can be set in one of two positions. The posterior position does not compress the spring. The anterior positions tenses the spring, anteriorly biasing the displaceable piston. In another, and preferred, embodiment of the present invention, a stilette is not used at all. Rather, the needle comes equipped with a catheter, preferably a blind end catheter, which runs from the tip of the needle, through both the displaceable and biasing pistons and out the posterior end of the syringe. The needle is inserted as before. However, when the epidural space is reached, the displaceable piston jumps forward, passing the anterior tip of the catheter into the epidural space tissue and thereby exposing the openings near the tip of the catheter and making them immediately available for the injection of anesthetizing fluids. This device is depicted in FIG. 9 hereof.

GB2226496 (Ziko Abdul Rahman Osman) teaches the working and construction of device for locating the epidural space. According thereto, the device comprises a rotor-containing chamber fitted on to the end of a syringe vessel and with the syringe needle projecting from the end of the chamber and in fluid-flow communication via the chamber with the syringe vessel. The negative pressure experienced at the tip of the needle as it enters the epidural space of a patient, in use, is transmitted via the needle to the chamber and causes the rotor to rotate. The rotation is visible through the transparent walls of the chamber and as soon as it is seen it tells the practitioner that he has found the epidural space. The device, consisting of rotor-containing chamber with needle projecting from one end thereof, and with the other end of the device fitting on to the syringe vessel in use, may be manufactured as a self-contained unit; or it may form an inherent extension of the syringe vessel and be constructed as part of the syringe from the outset. This device is depicted in FIG. 10 hereof.

ES 8706023 (Yuste Pascual Jose) teaches the working and construction of device for locating the epidural space. According thereto, an apparatus for the location of epidural, peridural or extradural spaces, which includes a needle or trocar for the injection of an isotonic saline solution by means of an infusion pump capable of providing a continuous flow, in such a manner that the various pressures produced when passing through the different anatomical structures are monitored until a sudden drop occurs which makes it possible to ascertain that the epidural space has been reached. Application The location of the epidural space, for the administration of chemical/pharmaceutical products, for diagnosis (diagnostics), and for analgesic or anaesthetic purposes. This device is depicted in FIG. 11 hereof.

In any of the above inventions disclosed, the stopping of further advancement of the needle is not addressed. Once after the reaching the epidural space, further forward movement of the hand has to be manually stopped. This is a safety concern as any slight inertial advancement of the hand may make the needle to move further, possibly causing dural puncture.

SUMMARY OF THE INVENTION

In a device according to at least one embodiment of the present invention the device provides for the automatic procedure of stopping the advancement of the needle after identification of the epidural space, even with further inertial forward movement of the hand.

The invention allows for pressurisation of the fluid in the syringe that leads to automatic injection of air or saline at the point of entry of the needle into the epidural space through differential friction at the tip of the needle, thereby causing the air or saline to be injected into the epidural space automatically.

One advantage of this invention is precise location of epidural space and simultaneous prevention of accidental dural puncture. Another objective of the invention is ergonomic, economically cost effective and safe technique.

The device of the invention is constructed on the technique of differential friction and has the advantage of applying the constant pressure on one single point i.e., on the piston of the syringe in attempt to inject air or saline. This results in two step-by-step actions i.e., simultaneous forward movement of the needle piercing through ligaments and building up of the pressure in the fluid contained the syringe, followed by simultaneous injecting of air or saline that pushes the dura further away and halting of the further movement of the needle even with a continuation of manual pressure on the piston of the syringe holding the wings which are located in a specialised way nearer to the hub of the needle.

One basic object of the invention is to locate the epidural space by the differential friction technique. Another object of the invention is to reduce the accidental dural puncture. Other desirable objectives are to reduce the complexity. Further objects of the invention are learnt by the description of the device, which form the part and parcel of this invention.

BRIEF DESCRIPTION OF THE DRAWINGS

The invention will now be described with reference to the accompanying drawings. In the drawings, like reference characters generally refer to the same parts throughout the different views. Also the drawings are not necessarily drawn to scale, emphasis instead generally being placed upon illustrating the technique of the invention.

Figure 1:
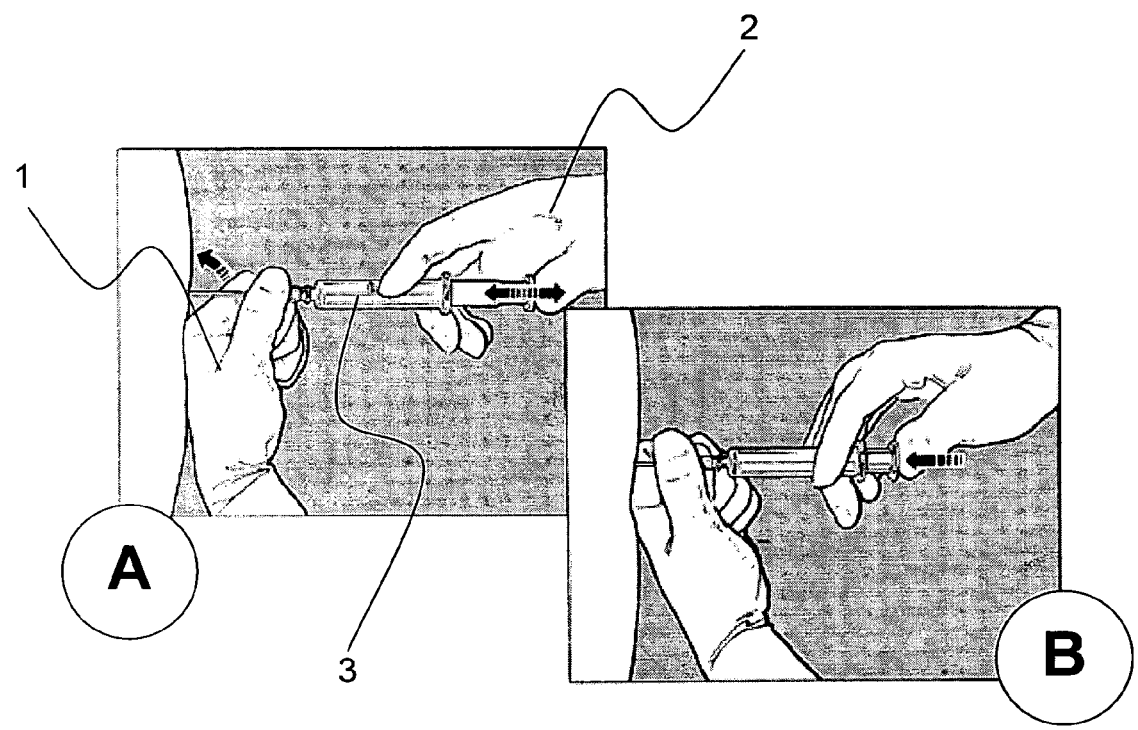
FIG. 1 depicts two stages of location of the epidural space by conventional technique wherein 1 indicates the hand used to give gentle forward movement of the needle, 2 is the hand used to push the piston and 3 is the saline with compressed air bubble.

Drawing A of FIG. 1 shows that the needle tip is in the ligaments and Drawing B of FIG. 1 shows that the needle tip is in the epidural space and injecting the air or saline to confirm the same.

Figure 2:
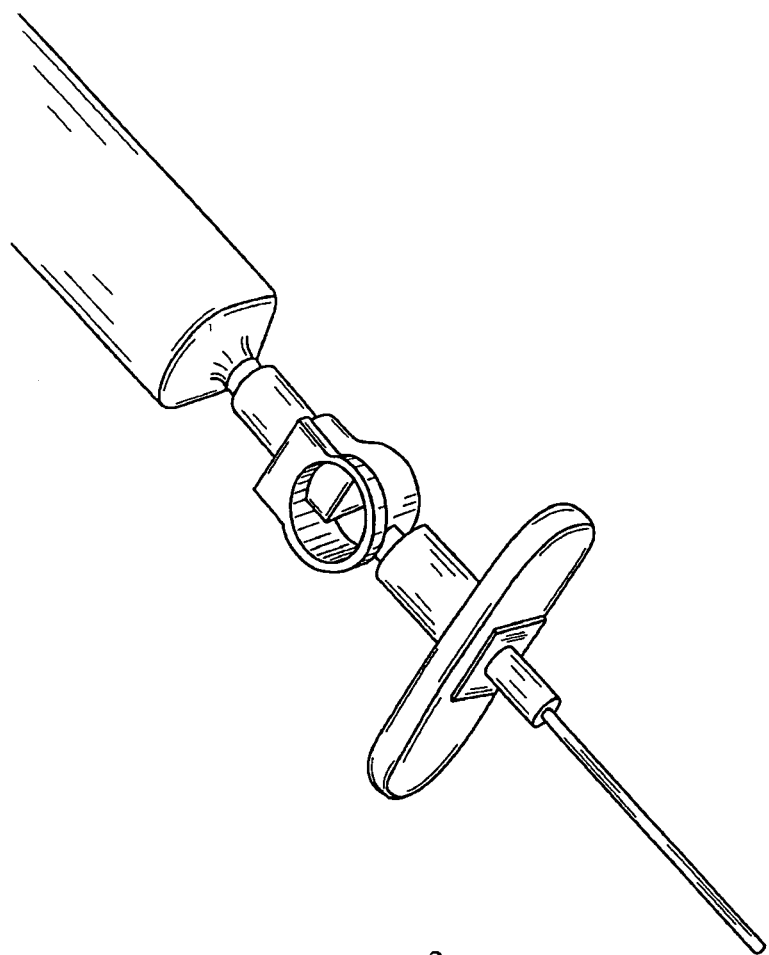

FIG. 2 depicts the device referred as prior-art in the specification.

Figure 3:
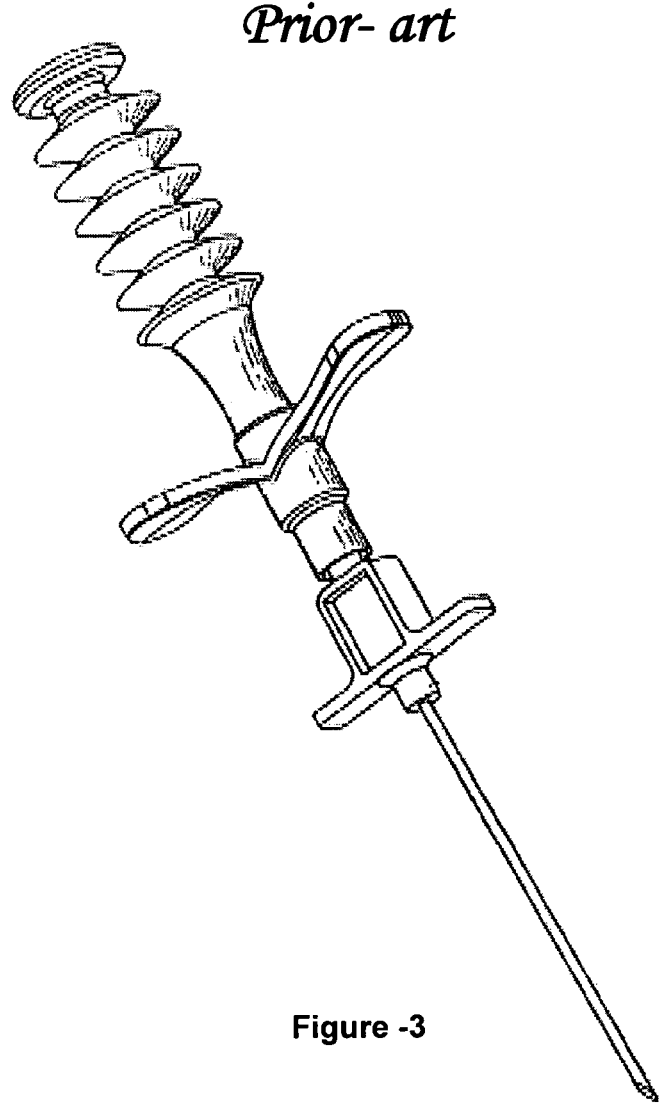

FIG. 3 depicts the device referred as prior-art in the specification.

Figure 4:
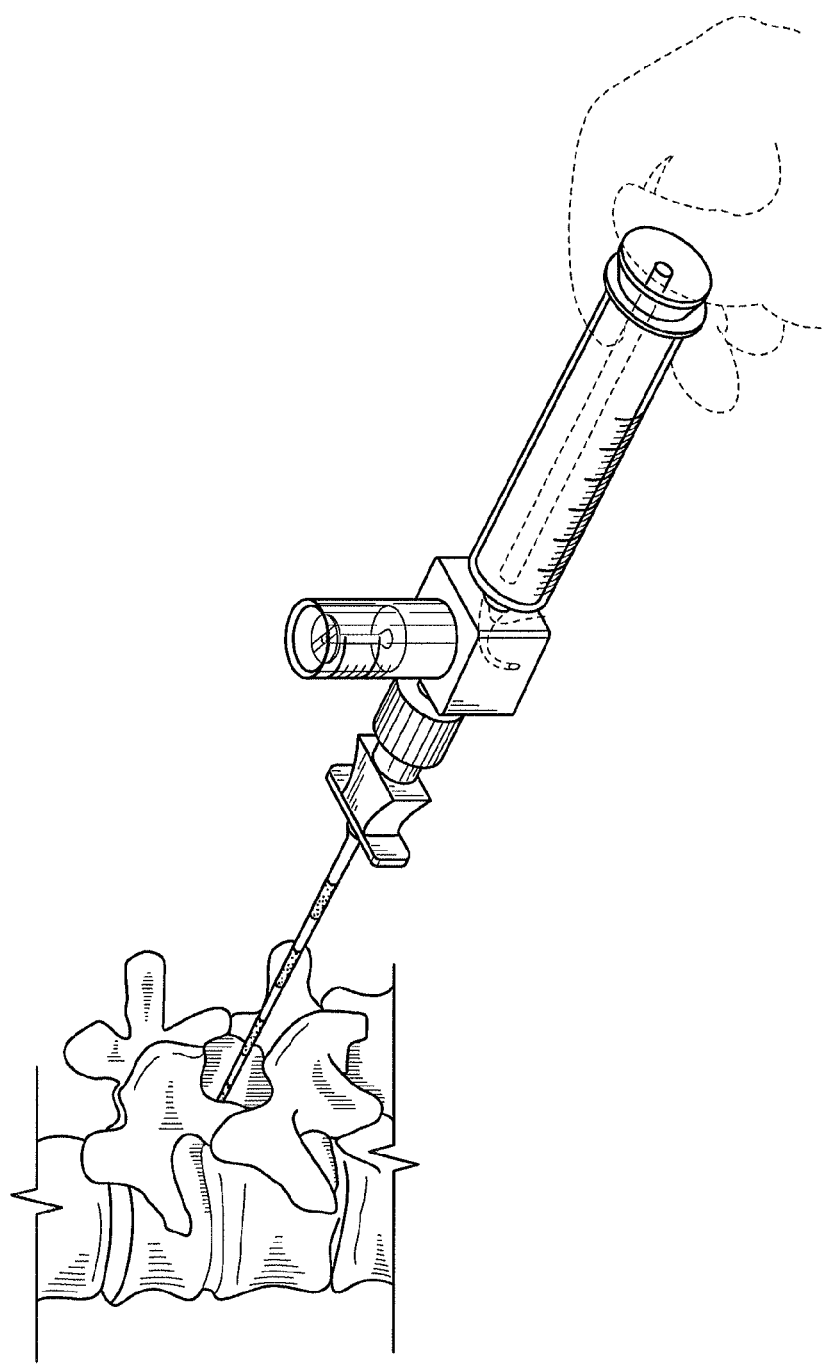

FIG. 4 depicts the device referred as prior-art in the specification.

Figure 5:
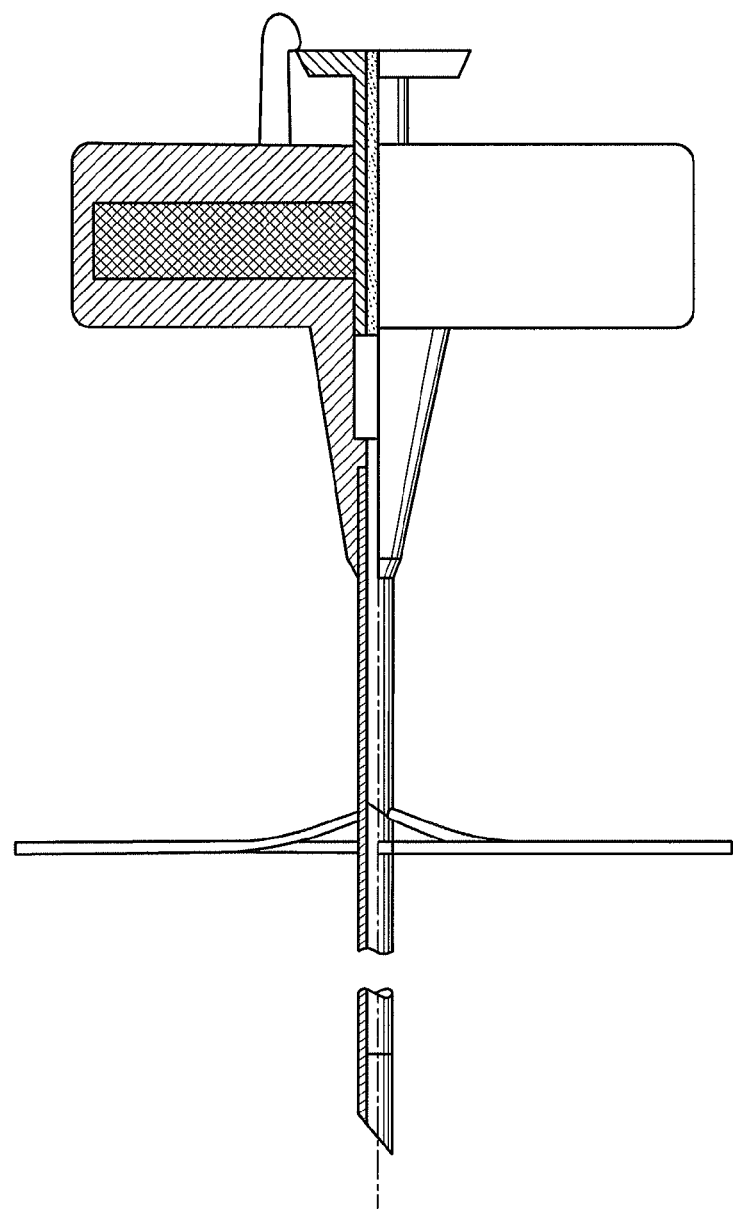

FIG. 5 depicts the device referred as prior-art in the specification.

Figure 6:
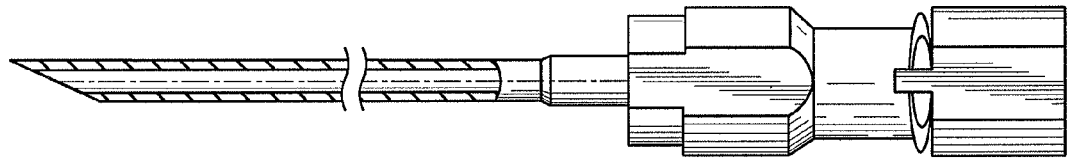

FIG. 6 depicts the device referred as prior-art in the specification.

Figure 7:
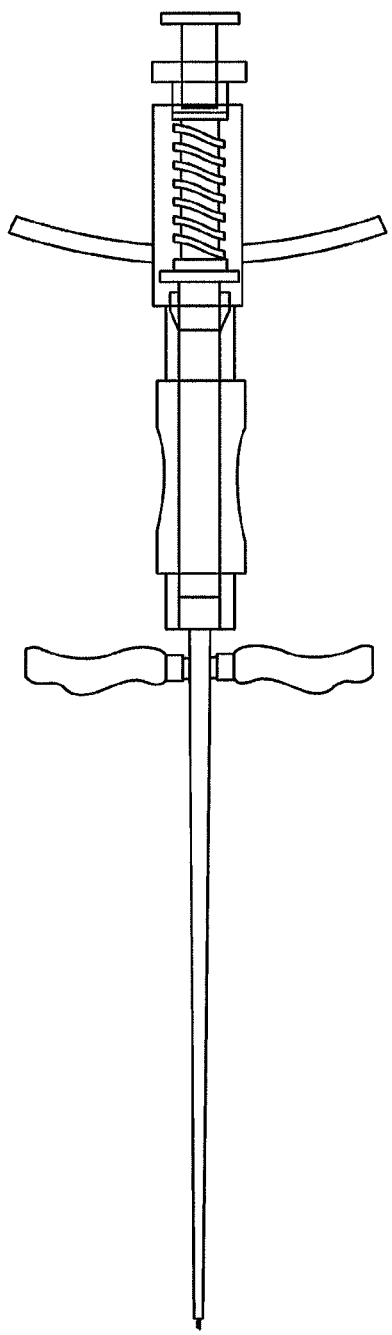

FIG. 7 depicts the device referred as prior-art in the specification.

Figure 8:
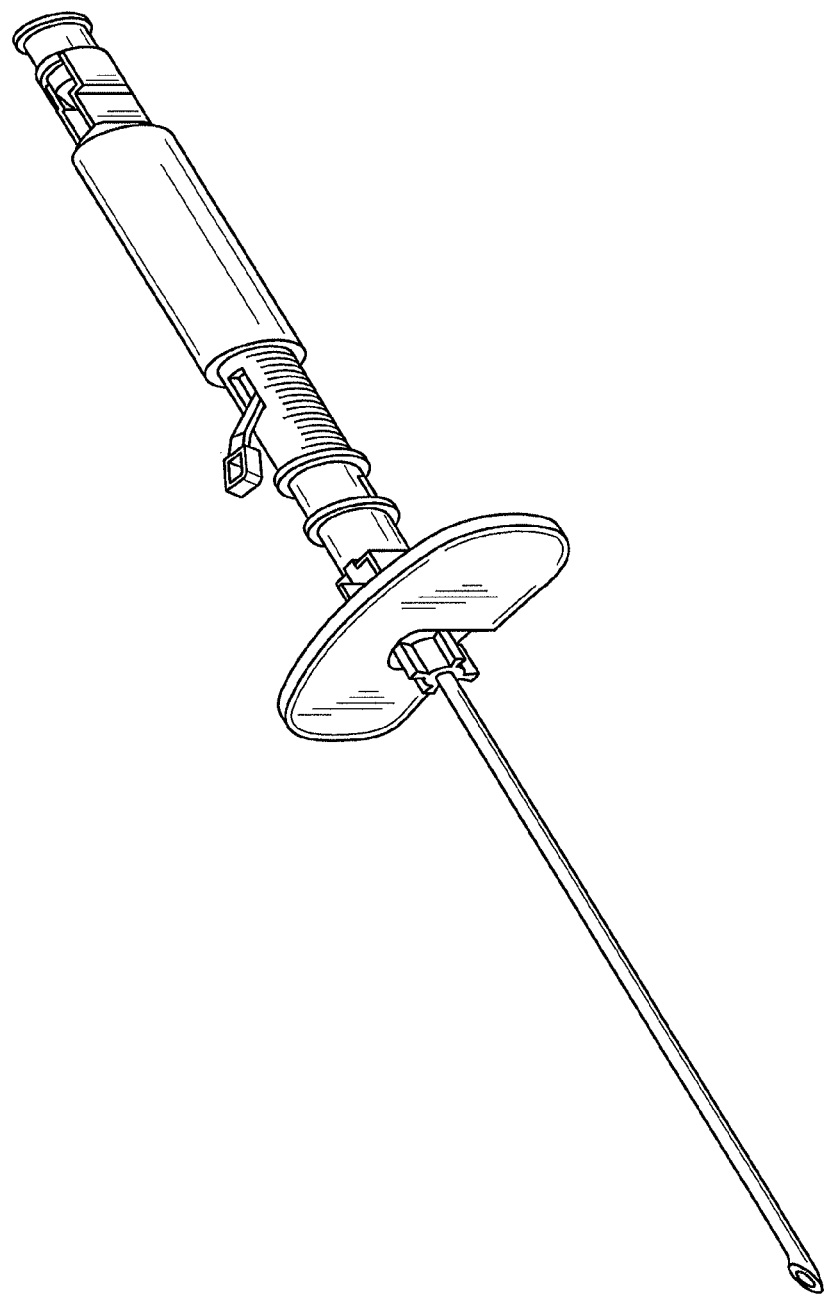

FIG. 8 depicts the device referred as prior-art in the specification.

Figure 9:
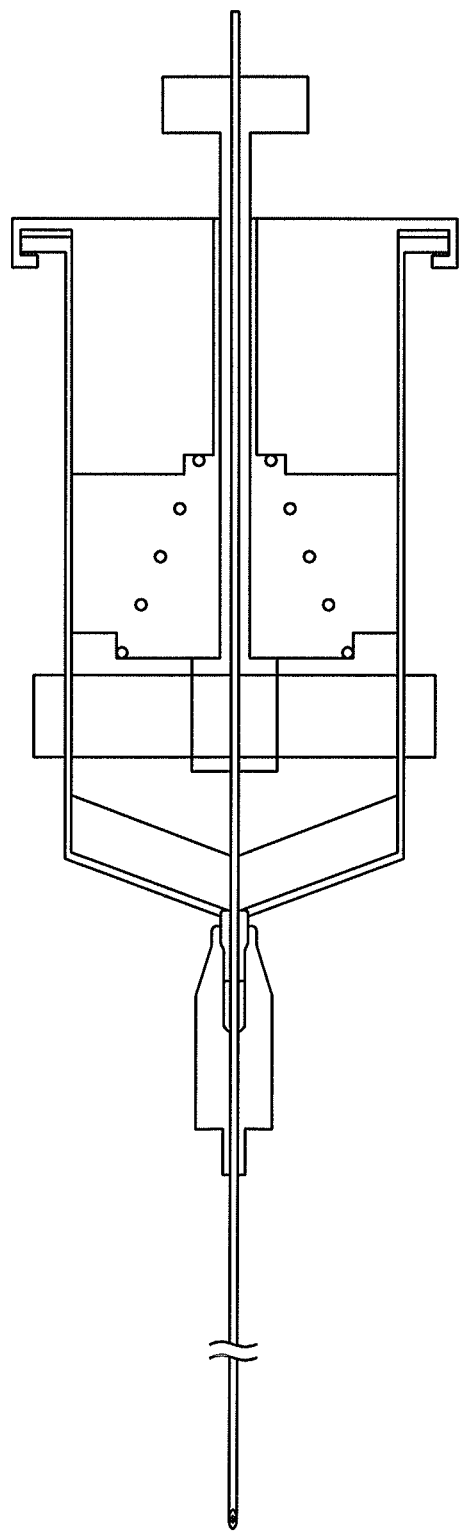

FIG. 9 depicts the device referred as prior-art in the specification.

Figure 10:
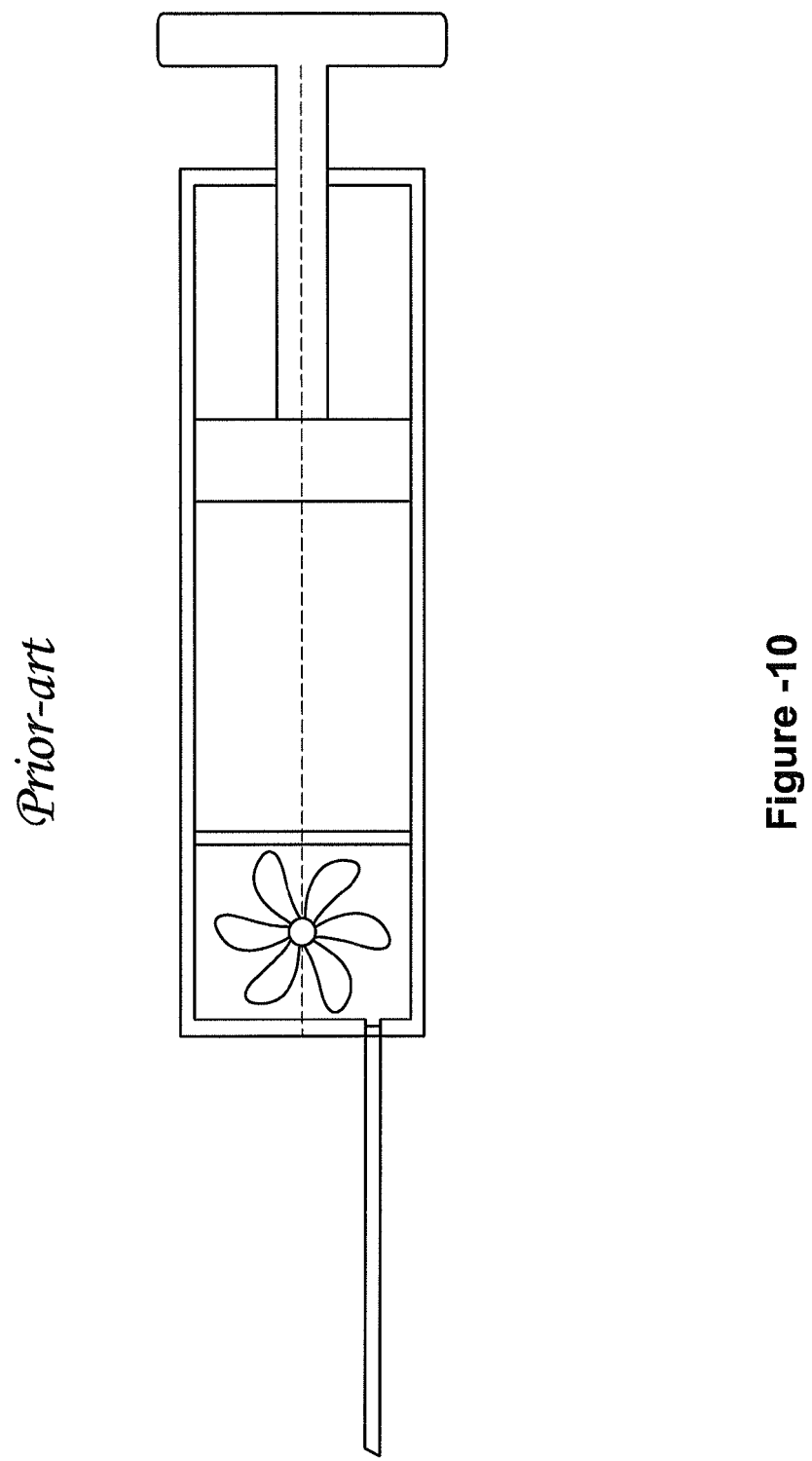

FIG. 10 depicts the device referred as prior-art in the specification.

Figure 11:
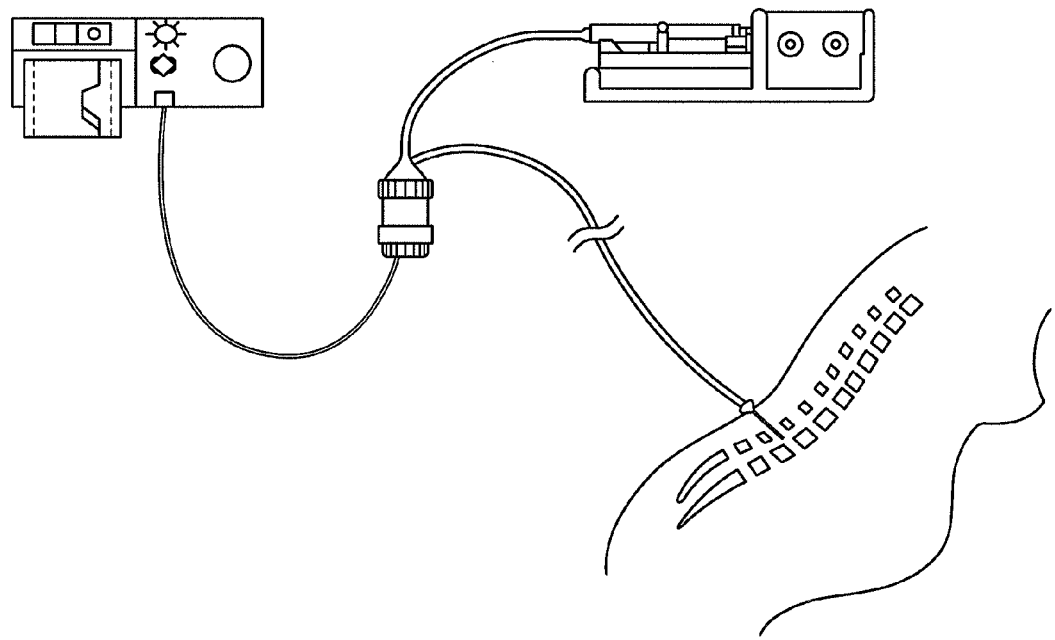

FIG. 11 depicts the device referred as prior-art in the specification.

Figure 12:
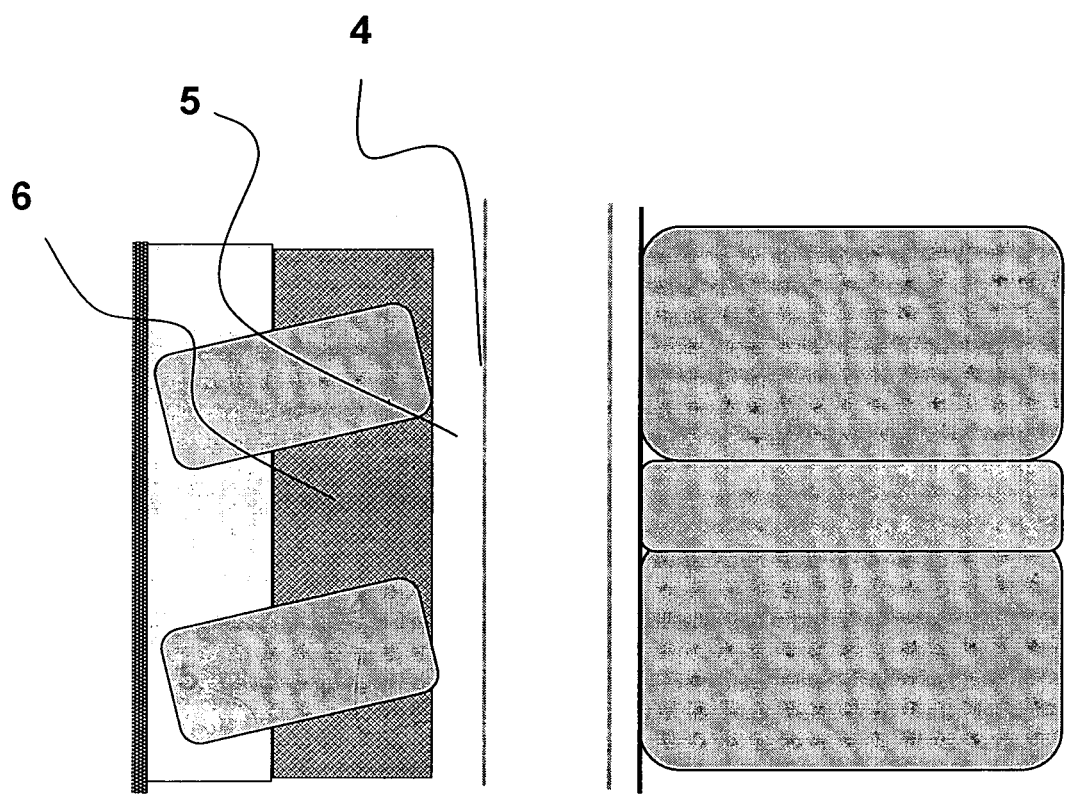

FIG. 12 depicts the anatomy of epidural space wherein 4 is the dural sac, 5 is the epidural space and 6 is the ligaments.

Figure 13:
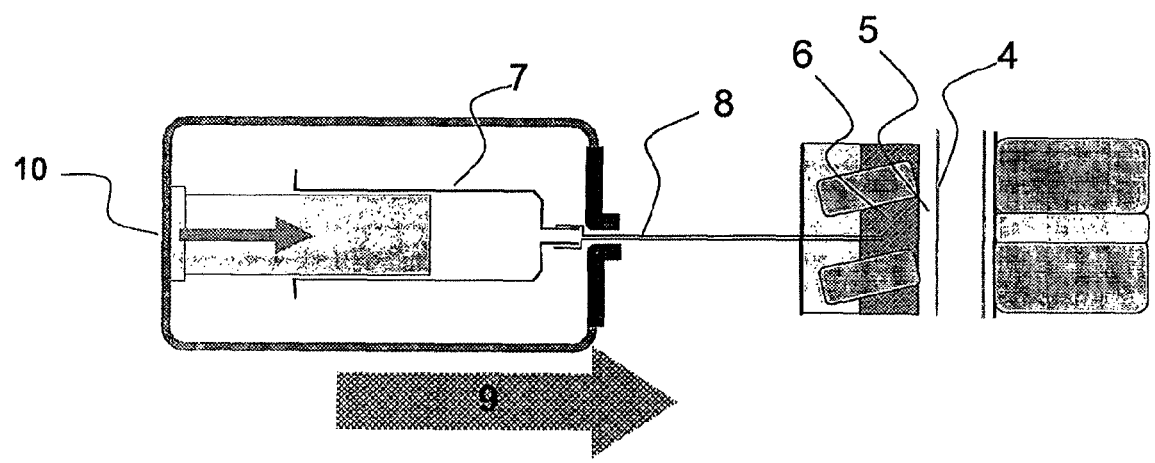

FIG. 13 depicts the differential friction technique stage 1, wherein 7 is the barrel of the syringe, 8 is the epidural needle, 9 is the direction of movement of the apparatus and 10 is the place and direction of application of constant manual force.

Figure 14:
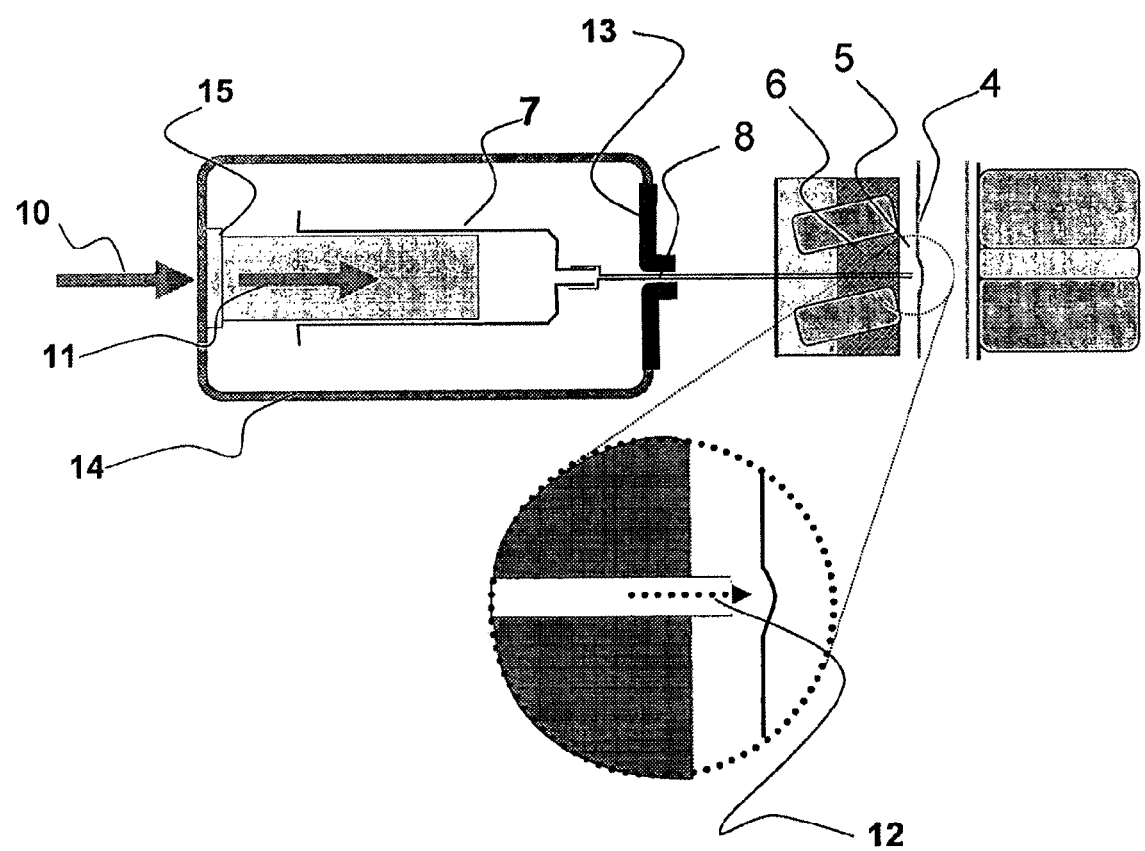

FIG. 14 depicts the differential friction technique in stage 2, wherein 11 is the isolated forward movement of the piston and 12 is the ejection of air or fluid into the epidural space. Furthermore, 13 is the wings placed on a separate block that moves over the body of the needle nearer hub, 14 is the frame connecting the wings block to the piston, and 15 is the piston.

Figure 15:
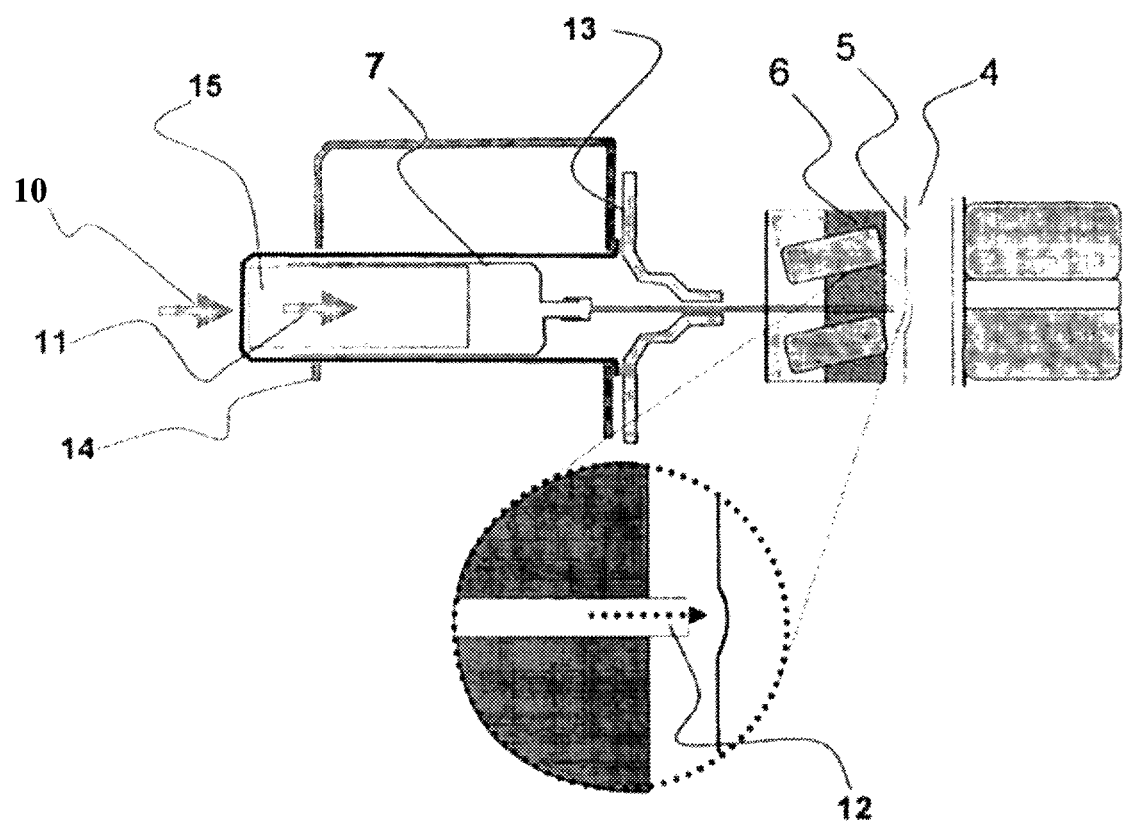

FIG. 15 depicts another ergonomically modified design of the apparatus for locating the epidural space with the same differential friction technique. The wings block in this design is suitable for withdrawal of the needle and re-direction of the apparatus in case it is needed.

Figure 16:
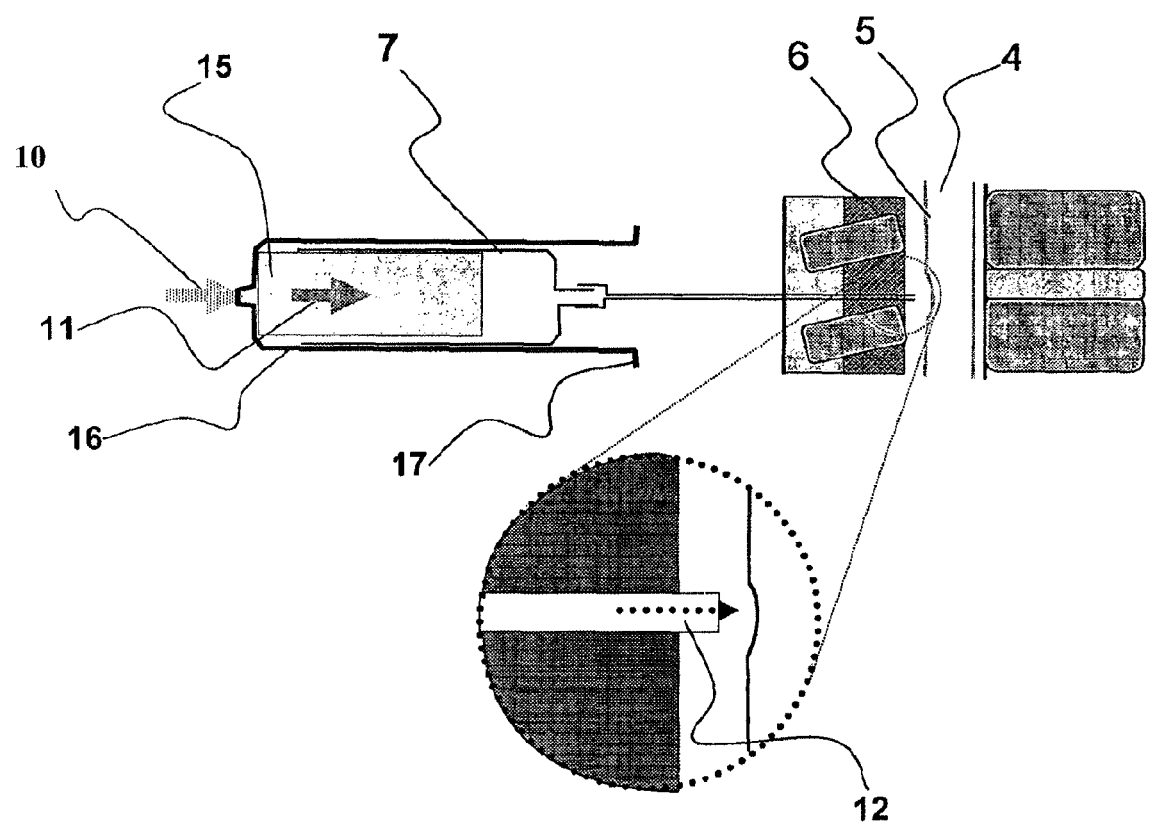

FIG. 16 depicts a practical method of eliciting differential friction technique of locating the epidural space by trimming the rim of the syringe and piston and encasing both of them by an empty barrel of a bigger syringe wherein 16 is the barrel of the bigger syringe. The rim of the bigger syringe acts as wings for hand grip wherein 17 is the rim of the bigger syringe. This design is useful for eliciting differential friction until actual device and further designs are manufactured.

Figure 17:
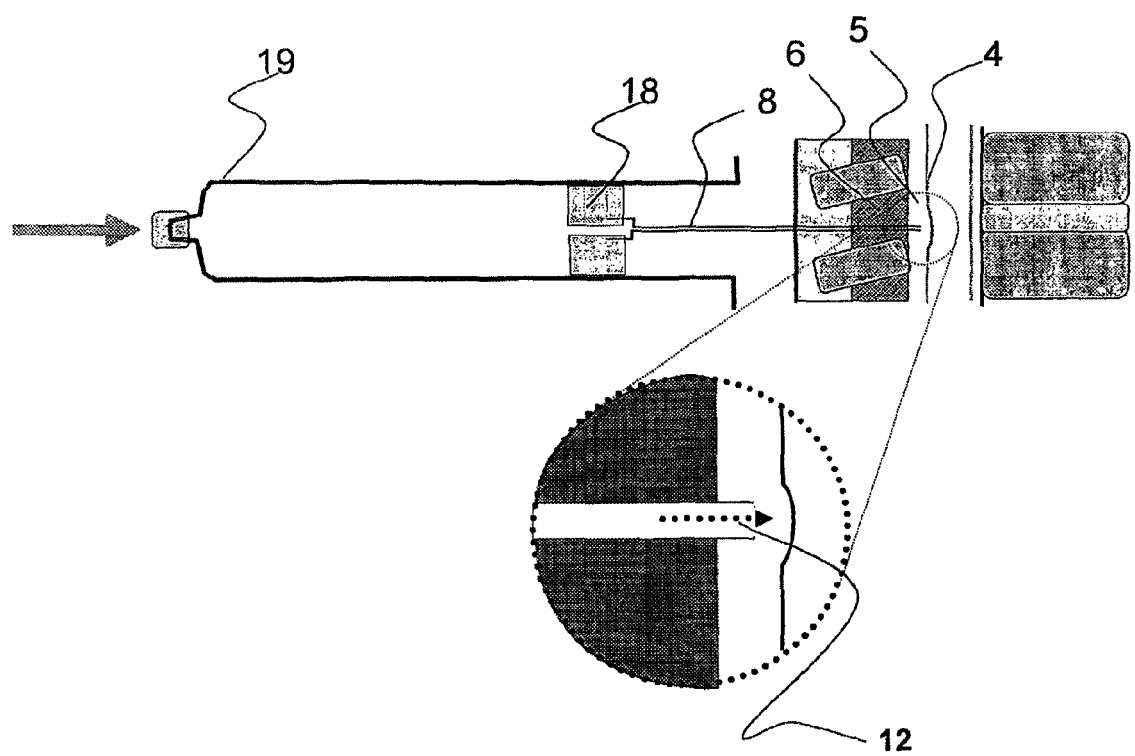

FIG. 17 depicts a design working on reverse piston method which is another ergonomic and practical modification of differential friction technique of locating the epidural space. The prototype depicts the piston head with a perforation mounted around the hub of the needle. The barrel which is closed after filling with fluid is shielded over, on to this combination of needle with piston head. This has the more ergonomic advantage. When the actual-device is manufactured, a filling port can be incorporated in the front portion of the barrel covered with air tight lid. This has economic advantage too, having cut short the need for handle of the piston. Wings, if needed can be incorporated in place of rim of the barrel depicted in this design wherein 18 is the perforated piston head mounted on to the hub of the needle and 19 is the reverse barrel.

Figure 18:
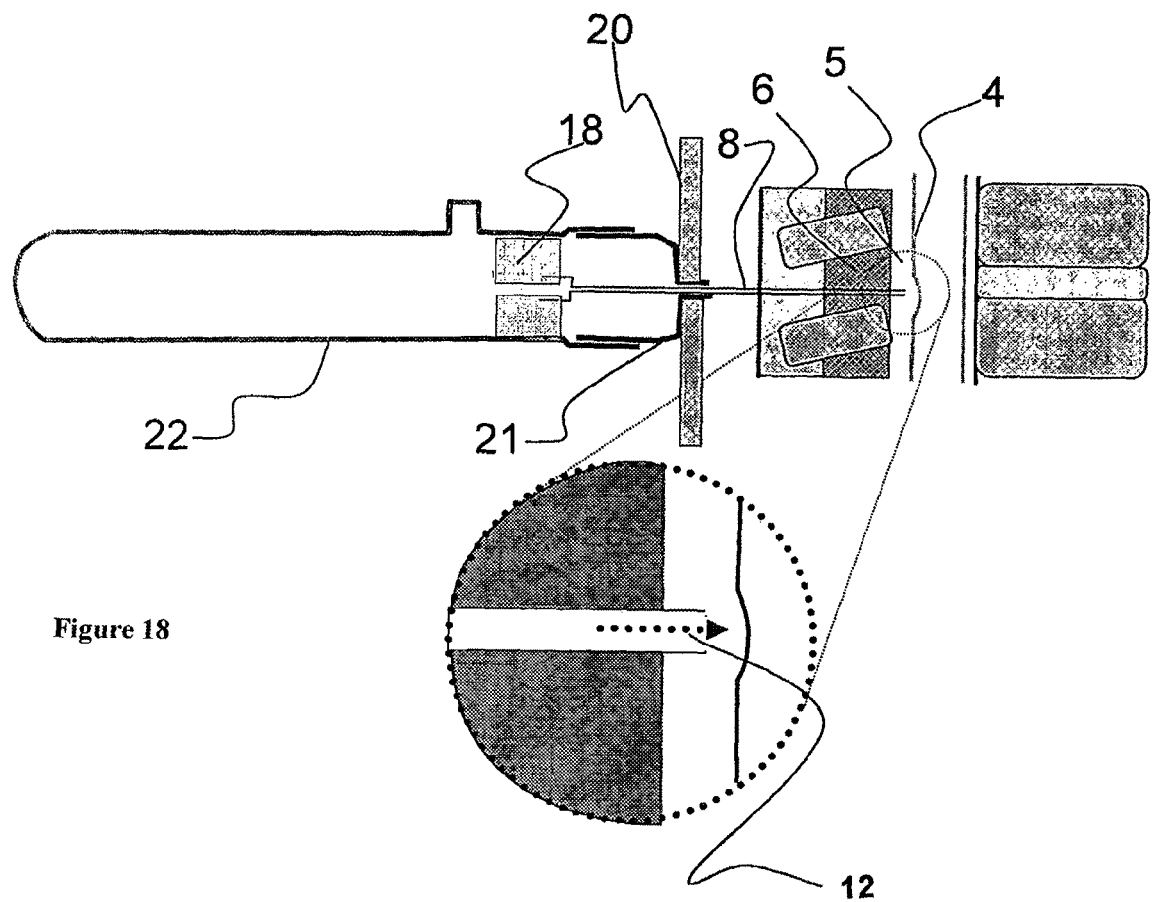

FIG. 18 depicts a near ultimate design of the device for locating epidural space by reverse piston method of differential friction technique of locating the epidural space. In this modification, the needle mounted with perforated piston head has a sleeve like component containing two optional wings mounted on to front part of the barrel wherein 20 is the wings, 21 is the front part of the barrel and 22 is the back part of the barrel, which is connected to its front part by means of a threading or latch.

Figure 19:
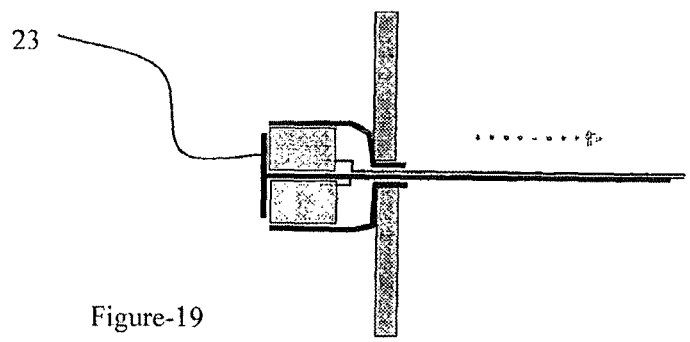

FIG. 19 depicts nothing but the front component of the apparatus mentioned in FIG. 18 depicting needle with wings block, mounted on front part of the barrel. The perforation in the piston head mounted around the needle hub permits placement of stylet 23. After location of epidural space, the rear part of the barrel is detached and a catheter can be inserted through this perforation.

Figure 20:
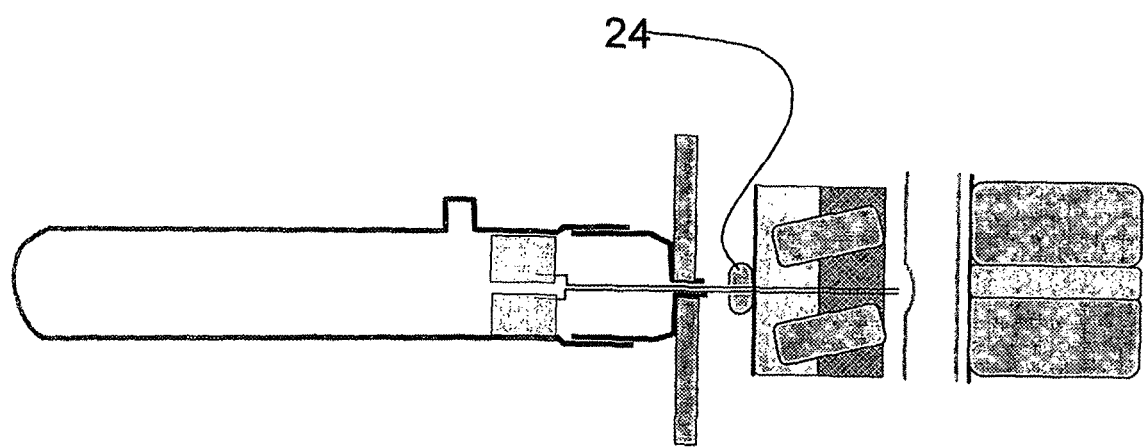

FIG. 20 depicts an elastic ring with pin point hole incorporated as a sleeve over the needle, which is adjusted to the point of entry of the needle on the skin wherein 24 is the elastic ring. This is supposed to be useful in providing added friction in paediatric patients with relatively softer ligaments.

Figure 21:
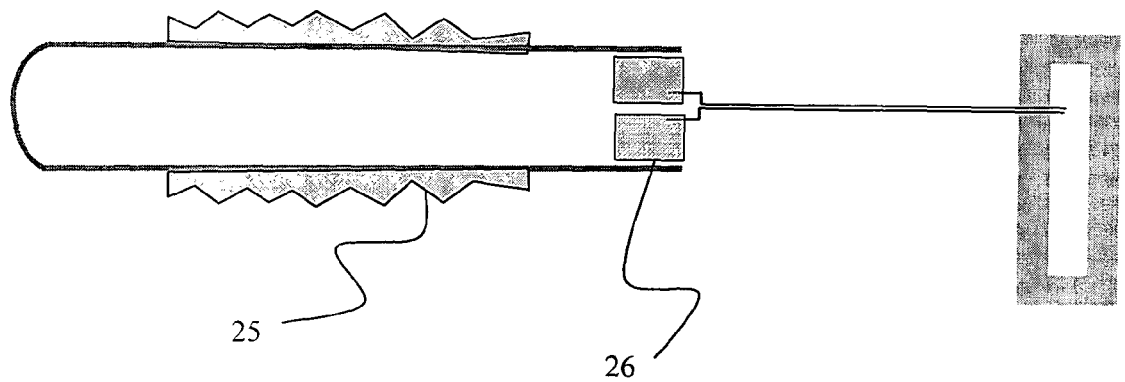

FIG. 21 depicts application of the differential friction technique to locate any other hollow cavity with firm to hard walls. Here a cannulated screw with hub mounted with perforated piston head is used in place of needle. The barrel with a hand grip is latched on to the outer surface of the piston head. Entry of the tip of the hollow screw into the bone causes ejection of fluid. This results in dislodgement of the latch wherein 25 is the hand grip and 26 is the latch. This design is useful in bone drilling, for giving some fluids into bone marrow cavity in certain situations.

DETAILED DESCRIPTION OF THE INVENTION

A preferred embodiment of the invention will now be described with reference to the accompanying drawings to understand the technique and the construction of the device.

An illustrative embodiment of the device for locating the epidural space is depicted in FIGS. 13 & 14 wherein 7 is the barrel of the syringe, 15 is the piston of the syringe inside the barrel 7, 8 is the wings that are placed near the hub of the needle but not mounted, onto the needle 8, 14 is the frame connecting, the wings to the back of the piston where the manual forward force on the wings is transmitted. In the figures, 10 is the forward force on the piston which initially causes movement of the entire apparatus (9 in FIG. 13) when the needle tip is in the ligaments 6. When the needle tip opens into epidural space, the movement of the needle and the barrel is halted by the friction offered by ligaments. In the figures, 5 is the epidural space into which the needle tip opens and ejects the fluid through needle.

In at least one embodiment, the present invention successfully addresses the shortcomings of the presently known epidural needle location indicator configurations by providing a device which facilitates the proper placement of the tip of the epidural needle in the epidural space in a manner which is largely automatic and which relies to a much lesser extent on the discretion and judgment of the anesthetist. It should be noted that use of the device according to the present invention is not limited to use in epidural anaesthesia. Rather, the device in FIG. 21, according to the present invention may be used whenever it is desired to locate the hollow cavities, with firm walls like that of bone and for locating epidural space through the ossified ligaments and 'bony walls of vertebral column. For illustrative purposes, only the device of the present invention is described below with reference to its application in epidural anaesthesia.

While explaining the basic differential friction technique, the construction, development and application of device or apparatus for locating the epidural space is now herewith depicted with figures and drawings.

A syringe containing air or saline in barrel 7 is taken and fixed to the epidural needle 8 is inserted into the deeper part of the spinal ligaments 6. A constant pressure 10 is applied on the back of the piston, 15 by means of wings 13 placed near the hub of the needle. These wings are placed near to the hub of the needle, but not mounted on to the needle 8 and are connected to the piston 15 by means of extensions forming frame 14. This gives a forward movement 9 of the entire apparatus and development of high pressure in the fluid contents of the barrel, initially causing the needle 8 to move forwards piercing through the ligaments 6. Once the tip of the needle 8 opens into the epidural space 5, the fluid 12 is forcibly ejected out due to loss of friction pushing the dura 4 away. At the same time, the relative high friction between the needle 8 and the ligaments 6 at this moment gives a "catch", halting the further forward movement of the tip of the needle 8 protecting the dura 4 from being punctured. This is essence of differential friction technique.

While administering the device of the present invention, the device works on the technique of differential friction. When the constant pressure 10 is applied on the piston 15 by means of wings 13, the friction to passage of fluid through the tip of the needle 8 is maximal when tip of the needle 8 is in the ligaments 6 and is minimal once it just comes out into epidural space 5. In the first instance, friction being maximal when the needle 8 is in the ligaments 6 causes the needle 8 to advance forward piercing through the ligaments 6. Once the tip of the needle 8 opens into epidural space 5 the friction becomes minimal causing the air or saline (fluid) 12 to be ejected forwards.

Once the needle opens into the epidural space, the friction of piston movement within the barrel becomes less than that encountered by the surface of needle passing though the ligaments. The continuing pressure on back of the piston now causes fluid ejection, halting the needle movement. This prevents the accidental dural puncture.

Other variations of the device are depicted in the corresponding figures enclosed. Of special relevance is reverse piston method where the needle hub itself has a mounted, perforated piston head. This is both effective ergonomic and economical as no extra piston shaft is needed and the perforation in the piston head allows passage of epidural catheter after detaching the barrel on locating the epidural space.

Another additional component optionally incorporated in the device is an elastic pinhole ring that encircles the epidural needle adjusted to the entry point of the needle into the skin. This provides additional friction in paediatric patients with softer intervertebral ligaments.

All features of each of the aspects of the present invention apply to all the other aspects mutatis mutandis. Variations, modifications, and other implementations of what is described herein will occur to those of ordinary skill in the art without departing from the spirit and the scope of the invention claimed. The same components of the invention may be re-arranged in an alternative design such as shown FIGS. 14-21 in the line draw views herein enclosed.

Accordingly, the invention is to be defined not by preceding illustrative embodiments but instead by the spirit and scope of the following claims.

I claim:

1. A device for locating a cavity within two walls including:
   a syringe including a syringe piston slideable in a first syringe barrel for discharging air or fluid contained in the first syringe barrel on forward movement of the syringe piston into the cavity, the first syringe barrel being attached to a hub of a needle cannula; and
   a rigid frame substantially encasing the syringe and having an opening for the needle cannula, wherein the rigid frame is connected to a back surface of the syringe piston and a force applied to the rigid frame is transferred to the back surface of the syringe piston by the rigid frame.

2. The device according to claim 1, wherein wings are attached to a front part of the rigid frame near the hub of the needle cannula.

3. A device for locating a cavity within two walls including:
   a syringe including a syringe piston slideable in a first syringe barrel for discharging air or fluid contained in the first syringe barrel on forward movement of the syringe piston into the cavity, the first syringe barrel being attached to a hub of a needle cannula; and
   a frame which at least in part encases the syringe and which is solely connected to the back of the syringe piston, wherein the frame is a second syringe barrel with a syringe tip end, the second syringe barrel being bigger than and mounted in reverse relative to the first syringe barrel and a syringe tip end being in connection with the back of the syringe piston.

4. A device according to claim 1, wherein a perforated elastic ring is mounted on the needle cannula.

5. A method of use of the device according to claim 1 by differential friction technique including:
   applying a continuous pressure to the rigid frame giving a forward movement to the entire device causing the needle cannula to pierce through the deeper parts of the first wall;
   ejecting the air or fluid from the first syringe barrel into the cavity once the tip of the needle cannula enters the cavity due to the loss of friction to the passage of the air or fluid through the tip of the needle cannula, thereby also pushing away the second wall;
   halting of the further forward movement of the tip of the needle catinula due to the friction between the needle cannula and the first wall being higher than the friction of forward movement providing safety against the accidental puncture of the second wall.

6. Use of a device according to claim 1 to locate the epidural space in the spinal column while safeguarding against puncture of the aural sac.

7. Use of a device according to claim 1 to locate bone marrow cavities.

8. The device according to claim 2, wherein the wings are coupled to the syringe piston via the rigid frame, and the force is applied to rigid frame by the wings.

9. The device according to claim 1, wherein the rigid frame is rectangular.

* * * * *

UNITED STATES PATENT AND TRADEMARK OFFICE
CERTIFICATE OF CORRECTION

PATENT NO.         : 8,715,234 B2                                                   Page 1 of 1
APPLICATION NO.    : 12/999473
DATED              : May 6, 2014
INVENTOR(S)        : Ravindar Bethi It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 404 days.

Signed and Sealed this

Twenty-ninth Day of September, 2015

Michelle K. Lee
*Director of the United States Patent and Trademark Office*